United States Patent

Reichel et al.

[11] Patent Number: 4,479,402
[45] Date of Patent: Oct. 30, 1984

[54] MICROTOME DRIVE

[75] Inventors: Artur Reichel, Wetzlar; Kurt Richter, Ehringshausen-Katzenfurt, both of Fed. Rep. of Germany

[73] Assignee: Ernst Leitz Wetzlar GmbH, Wetzlar, Fed. Rep. of Germany

[21] Appl. No.: 339,154

[22] Filed: Jan. 13, 1982

[30] Foreign Application Priority Data

Jan. 14, 1981 [DE] Fed. Rep. of Germany ... 8100644[U]

[51] Int. Cl.³ .................. F16H 35/00; F16D 21/02; B23D 5/08
[52] U.S. Cl. .................................. 74/625; 192/48.9; 192/67 P; 192/95; 83/915.5; 83/574
[58] Field of Search ............. 74/625; 192/48.9, 48.91, 192/67 P, 95; 83/915.5, 574

[56] References Cited

U.S. PATENT DOCUMENTS

| 754,757 | 3/1904 | Ellicott et al. | 74/625 |
| 2,918,011 | 12/1959 | McCray et al. | 192/95 |
| 2,949,817 | 8/1960 | Feindler | 83/915.5 |
| 3,315,540 | 4/1967 | Baumgartner | 192/95 |
| 3,491,638 | 1/1970 | Idlis | 83/915.5 |
| 3,869,030 | 3/1975 | Masaki | 192/95 |
| 4,285,496 | 8/1981 | Coles | 74/625 |

FOREIGN PATENT DOCUMENTS

| 238964 | 7/1964 | Fed. Rep. of Germany | 83/915.5 |
| 2321757 | 3/1974 | Fed. Rep. of Germany | 83/915.5 |

Primary Examiner—Leslie A. Braun
Assistant Examiner—Michael J. Gonet
Attorney, Agent, or Firm—Schwartz, Jeffery, Schwaab, Mack, Blumenthal & Koch

[57] ABSTRACT

A microtome actuable both manually and by a motor, with a single coupling element, whereby rotation of the hand wheel when the motor drive is engaged and thus the risk of injury by the manual grip are excluded. The coupling element is located in the hand wheel and is capable of locking in two positions by means of pulling and rotating, the respective positions establishing the manual or motor drive mode. The drive mode is made readily apparent from the outside by means of symbols. In the hand wheel, an equalizing weight for the object carriage is provided.

7 Claims, 2 Drawing Figures

MICROTOME DRIVE

BACKGROUND OF THE INVENTION

The present invention relates to a microtome drive having a drive shaft for movement of the object carriage, and more particularly to a microtome drive wherein the drive shaft carries a hand wheel for manual drive and a V belt pulley for motor drive and wherein coupling means are provided between the hand wheel and the V belt pulley.

In known microtomes, the movement and guidance of the preparation is effected by a drive shaft located on the microtome and rotated either by a hand wheel or by an electromotor. A disadvantage of these instruments consists of the fact that, with the drive motor engaged, the hand wheel also rotates, so that the protruding manual handle represents a significant risk of accident. The risk of accident is further enhanced at that moment when the motor drive is already running and the coupling between the motor drive and the drive shaft or the hand wheel is effected at the hand wheel or in its immediate vicinity, since the hand wheel is thereby abruptly set into a rotating motion, in part while the shifting operation is still in progress. Furthermore, with the instrument at rest, the type of drive engaged is not apparent, i.e., it cannot be visually ascertained whether the motor or the manual drive is engaged.

In a microtome proposed very recently, these disadvantages are eliminated. For this purpose, in order to control the type of drive in this device, two push rods supported in bearings parallel to the drive shaft are provided in a bushing mounted fixedly on the drive shaft. These push rods are each exposed to the action of a compression spring and are capable of alternating actuation, whereby on the one hand a follower is uncoupled from the hand wheel which is then not moved when the microtome is motor driven, and on the other hand, the follower engages in a recess in the hand wheel, when the microtome is to be operated by hand. This microtome drive requires a relatively large number of individual parts and is thus expensive.

Furthermore, in this instrument the weight equalization provided to compensate for the mass of the object carriage moving in the vertical direction must rest on the drive shaft.

SUMMARY OF THE INVENTION

It is therefore an object of the present invention to provide an improved microtome.

It is a further object of the invention to provide an improved microtome drive of the abovedescribed type in its mechanical structure.

Still another object of the invention resides in providing an effectively acting weight compensation for the mass of the object carriage.

In accomplishing the foregoing objects, there has been provided in accordance with the present invention a microtome drive for adjusting the position of an object carriage in a microtome, comprising a drive shaft rotatably mounted in the microtome; linkage means for adjusting the position of the object carriage in response to rotation of the drive shaft; a belt-driven pulley rotatably mounted on the drive shaft and adapted to be driven by a drive motor; a manual drive wheel fixedly attached to the drive shaft at a position adjacent to the belt-driven pulley; a ring member rotatably mounted on the manual drive wheel for rotation coaxially with respect to the manual drive wheel and the drive shaft, this ring member carrying thereon a manual gripping member; and means for selectively coupling the manual drive wheel alternatively to either the ring member for manual adjustment of the object carriage or to the belt-driven pulley for automatic adjustment of the object carriage. Preferably, the selective coupling means comprises a coupling element mounted in the manual drive wheel for displacement in a direction parallel to the axis of the drive shaft, and the coupling member includes a compression spring biasing the coupling element in the direction toward the belt-driven pulley.

In a particularly preferred embodiment, the microtome drive further includes an equalizing weight for the object carriage arranged in the manual drive wheel, and the coupling element is rotatably mounted and comprises on its end facing the belt-driven pulley a locking projection and on its opposite end a locking cam offset with respect to said locking projection. The belt-driven pulley comprises a locking recess adapted to engage the locking projection upon displacement of the coupling element toward the pulley, and the ring member comprises a locking recess adapted to engage the locking cam when the coupling element is displaced away from the pulley and rotated by an angle equal to the offset.

Further objects, features and advantages of the invention will become apparent from the detailed description of preferred embodiments which follows when considered together with the attached figures of drawings.

DETAILED DESCRIPTION OF PREFERRED EMBODIMENTS

Figure 1:
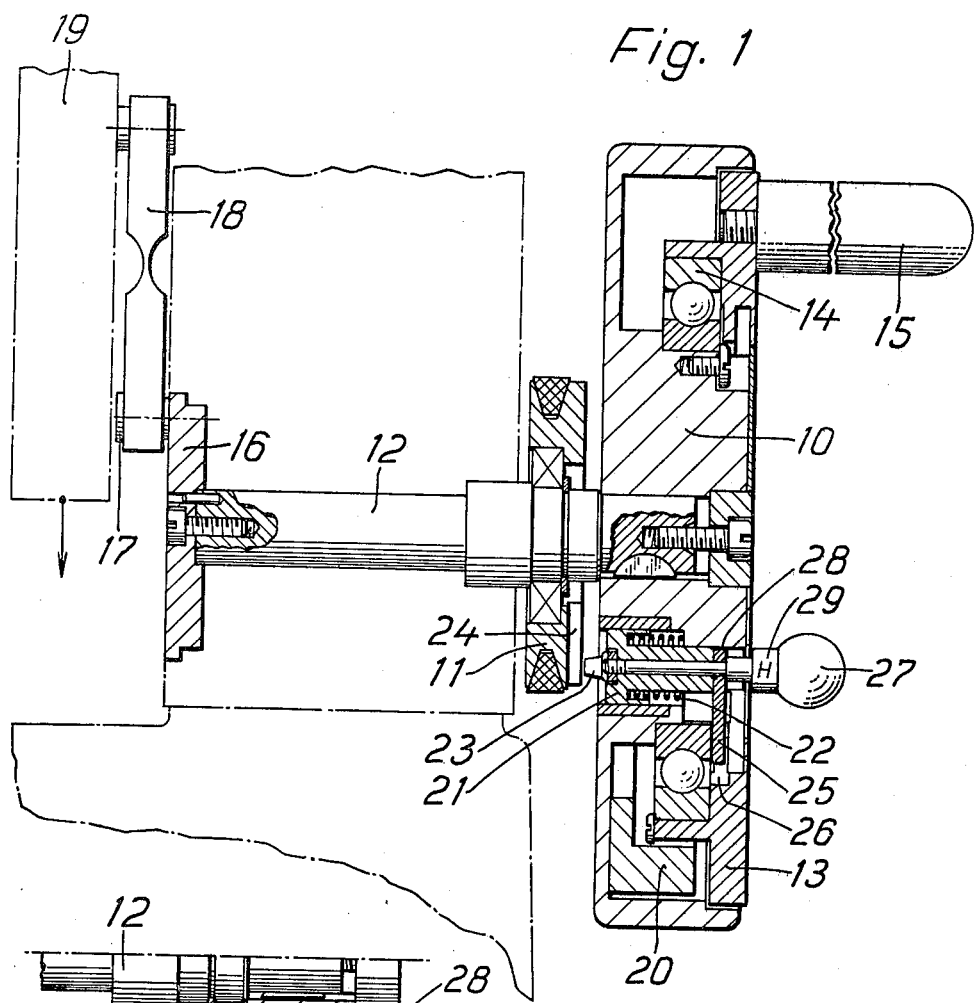
FIG. 1 is a lateral elevation, partly in section and partly broken away, of the microtome drive according to the invention in the manual drive position.
Figure 2:
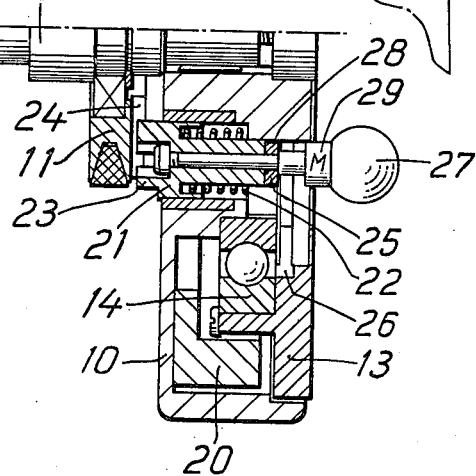
FIG. 2 is a partial view of the microtome drive in the motor drive position, again partly in section.

According to the invention, for establishing the type of drive, a ring having a manual grip and a coupling element, which is displaceable parallel to the drive shaft and subject to the action of a compression spring, is rotatably located in the hand wheel. The coupling element penetrates the ring and the hand wheel and makes it possible to selectively couple either the ring with the hand wheel or the hand wheel with the V belt pulley. In order to change from manual to motor operation, only the actuation of a single coupling element is required as a result of this design, and the entire arrangement comprises few structural parts. The weight compensation for the object carriage in this manner constitutes a part of the hand wheel.

In one preferred embodiment of the invention, the coupling element is located rotatably in the ring and has at its end facing the V belt pulley a locking projection and on the other end a locking cam offset with respect to the locking projection. The locking projection may be brought into engagement with a recess in the V belt pulley, and the locking cam may be brought into engagement with a groove in the hand wheel. In order to securely couple the ring with the hand wheel for manual driving, it is sufficient to pull the coupling element in the axial direction out from the ring, against the effect of the compression spring, and to rotate it by the offset angle between the locking cam and the locking projection, which for example, may amount to 90°. In the process, the locking projection is pulled from the recess in the V belt pulley, thereby releasing its connection therewith. Upon release of the coupling element, the locking cam thereof engages the groove in the hand wheel, thereby coupling the latter with the ring. In order to shift to motor drive, the coupling element is pulled out and rotated in the opposite direction until, following the attainment of the offset angle, the locking cam slides out from the groove of the hand wheel. Upon its release, the coupling element is displaced axially under the action of the compression spring, so that its locking projection is able to engage the recess of the V belt pulley. In this manner, the decoupling of the ring from the hand wheel is insured and the connection of the hand wheel with the V belt pulley effected.

In order to prevent play in the locked state between the locking cam and the groove and between the locking projection and the recess, and to facilitate engagement, both the locking projection and the locking cam have bevelled surfaces.

For easy gripping, the coupling element is equipped with a spherical knob as the handle. This knob protrudes from the frontal surface of the ring.

Further details of the invention will become apparent from the description hereinafter of a preferred embodiment of the invention which is schematically illustrated in the drawings.

Referring now to the drawings, the microtome drive shown in the figures comprises essentially a hand wheel 10 and a V belt pulley 11, mounted adjacently to each other on a drive shaft 12. The V belt pulley 11 is mounted for free rotation on drive shaft 12. In the fixedly mounted hand wheel 10, a ring 13 is supported in a freely rotating manner by means of a ball bearing 14. The ring has a manual grip 15 on its outer frontal side. Rigidly fastened to the shaft 12 on the end facing away from the rotatingly mounted V belt pulley 11 is a clamping washer 16 which by means of an eccentrically positioned bolt 17 engages a connecting rod 18, which moves the object carriage 19 linearly in the known manner. In FIG. 1, the object carriage 19 occupies its terminal position.

In the hand wheel 10, a compensating weight 20 is provided, to equalize the weight of the object carriage 19.

Parallel to the drive shaft 12, a cylindrical coupling element 21 which penetrates the hand wheel 10 and the ring 13 is rotatably supported. The coupling element 21 is surrounded partially by a compression spring 22, biasing it in the direction of the V belt pulley 11. At its end facing the V belt pulley 11, the coupling element 21 is provided with a locking projection 23, capable of engaging a corresponding recess 24 in the V belt pulley 11. In the area of the other end of the shaft of the coupling element 21, a locking cam 25 is provided which is offset by 90° with respect to the locking projection 23 and is capable of engaging a groove 26 in the hand wheel 10. Both the locking projection 23 and the locking cam 25 have bevelled surfaces.

In the position for manual drive shown in FIG. 1, the locking projection 23 is located outside the recess 24 in the V belt pulley 11, and there is therefore no active connection between the V belt pulley 11 and the hand wheel 10. In order to shift to motor drive, the coupling element 21 is pulled out, using a spherical knob 27 provided thereon as a handle, rotated in the counterclockwise direction by 90° and released. Under the effect of the compression spring 22, the coupling element 21 is displaced in the direction of the V belt pulley 11 and abuts against the frontal side of the latter with its locking projection 23, while the locking cam 25 slides into a free space 28 of the hand wheel 10. Upon the actuation of the motor drive, the locking projection 23 engages the recess 24 of the V belt pulley 11 after less than a full revolution of the latter, whereby the connection between the hand wheel 10 and the V belt pulley 11, and thus between the V belt pulley and the drive shaft 12, is established. The ring 13 may now freely rotate in the hand wheel 10.

The drive modes may be made readily apparent by markings on the spherical knob 27 and corresponding symbols, not shown, on the ring.

What is claimed is:

1. A microtome drive for adjusting the position of an object carriage in a microtome, comprising:
    a drive shaft rotatably mounted in the microtome;
    linkage means for adjusting the position of the object carriage in response to rotation of said drive shaft;
    a belt-driven pulley rotatably mounted on said drive shaft and adapted to be driven by a drive motor;
    a manual drive wheel fixedly attached to said drive shaft at a position adjacent to said belt-driven pulley;
    a ring member rotatably mounted on said manual drive wheel for rotation coaxially with respect to said manual drive wheel and said drive shaft, said ring member carrying thereon a manual gripping member; and
    means for selectively coupling said manual drive wheel alternatively to either said ring member for manual adjustment of the object carriage or to said belt-driven pulley for automatic adjustment of the object carriage.

2. A microtome drive according to claim 1, wherein said selective coupling means comprises a coupling element mounted in said manual drive wheel for displacement in a direction parallel to the axis of said drive shaft.

3. A microtome drive according to claim 2, wherein said coupling element further comprises a compression spring biasing said coupling element in the direction toward said belt-driven pulley.

4. A microtome drive according to claim 1, further comprising an equalizing weight for the object carriage arranged in said manual drive wheel.

5. A microtome drive according to claim 3, wherein said coupling element is rotatably mounted and comprises, on its end facing said belt-driven pulley, a locking projection and on its opposite end a locking cam offset with respect to said locking projection, wherein said belt-driven pulley comprises a locking recess adapted to engage said locking projection upon displacement of said coupling element toward said pulley, and wherein said ring member comprises a locking recess adapted to engage said locking cam when said coupling element is displaced away from said pulley and rotated by an angle equal to said offset.

6. A microtome drive according to claim 5, wherein both said locking projection and said locking cam have bevelled surfaces.

7. A microtome drive according to claim 5, wherein said coupling element further comprises a spherical knob as a manual grip located at its end opposite from said pulley.

* * * * *